United States Patent
Tagami et al.

(10) Patent No.: US 9,931,241 B2
(45) Date of Patent: Apr. 3, 2018

(54) STEAM-GENERATIVE WARMING DEVICE

(75) Inventors: Kyouko Tagami, Sumida-ku (JP);
Katsutoshi Hara, Sumida-ku (JP);
Ichiro Sakamoto, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 289 days.

(21) Appl. No.: 13/702,207

(22) PCT Filed: Jun. 8, 2011

(86) PCT No.: PCT/JP2011/063175
§ 371 (c)(1),
(2), (4) Date: Dec. 11, 2012

(87) PCT Pub. No.: WO2011/155542
PCT Pub. Date: Dec. 15, 2011

(65) Prior Publication Data
US 2013/0079851 A1    Mar. 28, 2013

(30) Foreign Application Priority Data

Jun. 9, 2010   (JP) .................................. 2010-132499

(51) Int. Cl.
*A61F 7/02*  (2006.01)
*A61F 7/03*  (2006.01)
*A61F 7/00*  (2006.01)

(52) U.S. Cl.
CPC ............... *A61F 7/03* (2013.01); *A61F 7/034* (2013.01); *A61F 2007/0062* (2013.01); *A61F 2007/0226* (2013.01); *A61F 2007/0261* (2013.01)

(58) Field of Classification Search
CPC ...... A61F 2007/0062; A61F 2007/0226; A61F 2007/0261; A61F 7/03; A61F 7/032; A61F 7/034; A61B 18/06
See application file for complete search history.

(56) References Cited

U.S. PATENT DOCUMENTS 6,299,885 B1    10/2001    Yamasaki et al.
6,471,997 B1 *  10/2002    Breton et al. ................. 424/725
(Continued)

FOREIGN PATENT DOCUMENTS

CN    101252923 A    8/2008
EP    1 147 752 A1   10/2001
(Continued)

OTHER PUBLICATIONS

WebMD, Cayenne Pepper (Capsicum): Uses, Side Effects, Interactions and Warnings, Apr. 1998, pp. 1-2.*
(Continued)

*Primary Examiner* — Kaitlyn Smith
*Assistant Examiner* — Yasamin Ekrami
(74) *Attorney, Agent, or Firm* — Sterne, Kessler, Goldstein & Fox P.L.L.C.

(57) ABSTRACT

A steam-generative warming device 10 having a steam generating element 30 that releases steam in association with heat generation accompanying the oxidation of an oxidizable metal. The steam generative warming device 10 contains a capsaicin analog and a menthol in a capsaicin analog/menthol mass ratio of 1/300 to 1/20000. It is preferred that the capsaicin analog be present in an element adapted to be brought into direct contact with the user's skin and the menthol be present in an element adapted not to be brought into contact with the user's skin.

12 Claims, 2 Drawing Sheets

(56) References Cited

U.S. PATENT DOCUMENTS

| | | | |
|---|---|---|---|
| 6,629,964 B1 | 10/2003 | Ono et al. | |
| 7,972,635 B2 * | 7/2011 | Seabrook et al. | 424/736 |
| 8,945,072 B2 | 2/2015 | Oda et al. | |
| 2002/0045923 A1 * | 4/2002 | Tone et al. | 607/96 |
| 2003/0203015 A1 * | 10/2003 | Aledo | A61F 13/0203 424/445 |
| 2004/0180081 A1 * | 9/2004 | Angel et al. | 424/449 |
| 2004/0202707 A1 * | 10/2004 | Muller | 424/449 |
| 2005/0281881 A1 | 12/2005 | Woeller et al. | |
| 2006/0093656 A1 | 5/2006 | Muta et al. | |
| 2006/0198806 A1 * | 9/2006 | Reilly | 424/70.13 |
| 2006/0222690 A1 * | 10/2006 | Bley | 424/448 |
| 2007/0020412 A1 | 1/2007 | Kumamoto et al. | |
| 2007/0190009 A1 * | 8/2007 | Guentert et al. | 424/70.6 |
| 2007/0233211 A1 * | 10/2007 | Galer | 607/96 |
| 2008/0020996 A1 | 1/2008 | Singh et al. | |
| 2008/0039749 A1 * | 2/2008 | Kopanic et al. | 601/46 |
| 2008/0058362 A1 * | 3/2008 | Singh et al. | 514/282 |
| 2009/0112283 A1 * | 4/2009 | Kriksunov et al. | 607/46 |
| 2009/0191249 A1 * | 7/2009 | Adelakun | 424/405 |
| 2009/0202634 A1 * | 8/2009 | Jans et al. | 424/468 |
| 2009/0258843 A1 * | 10/2009 | Cantrell et al. | 514/161 |
| 2010/0023099 A1 | 1/2010 | Hidaka et al. | |
| 2010/0099766 A1 * | 4/2010 | Zhang et al. | 514/567 |
| 2010/0120780 A1 * | 5/2010 | Singh | 514/250 |
| 2010/0217170 A1 | 8/2010 | Tsuru et al. | |
| 2011/0190714 A1 * | 8/2011 | Oda | A61F 7/03 604/291 |

FOREIGN PATENT DOCUMENTS

| | | | | |
|---|---|---|---|---|
| EP | 2177183 A1 * | 4/2010 | | A61F 7/034 |
| JP | 08-081370 A | 3/1996 | | |
| JP | 11-035475 A | 2/1999 | | |
| JP | 11-342147 | 12/1999 | | |
| JP | 2002-29993 A1 | 1/2002 | | |
| JP | 2002-078728 A | 3/2002 | | |
| JP | 2003-210509 A | 7/2003 | | |
| JP | 2003-250829 A | 9/2003 | | |
| JP | 2003-327527 A | 11/2003 | | |
| JP | 2004-208921 A | 7/2004 | | |
| JP | 2005-087719 A | 4/2005 | | |
| JP | 2005-206573 A | 8/2005 | | |
| JP | 2006-513194 A | 4/2006 | | |
| JP | 2007-136053 A | 6/2007 | | |
| JP | 2008-220943 A | 9/2008 | | |
| JP | 2009-035723 A | 2/2009 | | |
| JP | 2010-158507 A | 7/2010 | | |
| JP | 2011-020991 A | 2/2011 | | |
| SU | 1790400 A3 | 1/1993 | | |
| WO | WO 2004/047820 A1 | 6/2004 | | |
| WO | WO 2004047820 A1 * | 6/2004 | | |
| WO | WO 2005115325 A1 * | 12/2005 | | A61K 7/48 |
| WO | WO 2007126430 A1 * | 11/2007 | | |

OTHER PUBLICATIONS

International Search Report (ISR) for PCT/JP2011/063175, I.A. fd: Jun. 8, 2011, dated Jul. 12, 2011 from the Japanese Patent Office, Tokyo, Japan.

International Preliminary Report on Patentability (IPRP), Chapter I of the Patent Cooperation Treaty, including the Written Opinion for PCT/JP2011/063175, I.A. fd: Jun. 8, 2011, dated Jan. 15, 2013, from the International Bureau of WIPO, Geneva, Switzerland.

Excerpted file history of U.S. Appl. No. 13/122,616, downloaded from the United States Patent and Trademark Office, Alexandria, VA.

Tsuruda, PR et al., "Coiled coils direct assembly of a cold-activated TRP channel," Neuron, Jul. 2006; 51(2): 201-212, Cell Press, Cambridge, MA.

Extended European search report including the supplementary European search report and European search opinion, for EP Appl. No. 11792499.3, dated Mar. 20, 2017, European Patent Office, Munich, Germany.

* cited by examiner

STEAM-GENERATIVE WARMING DEVICE

TECHNICAL FIELD

The present invention relates to a steam generative warming device that imparts steam and warmth to the body of a user.

BACKGROUND ART

In the field of warming devices utilizing heat generation by oxidation of iron powder, incorporation of capsaicin or menthol into warming devices is known. For example, patent literature 1 below describes a warming device including an air permeable bag containing a heat generative material capable of heat generation on contact with air and a plaster layer on the skin contact side of the bag, the plaster layer containing an effective ingredient of plaster, such as a *capsicum* extract or l-menthol.

Patent literature 2 below discloses a warming sheet including a pressure sensitive adhesive layer and a heat generating layer containing a heat generating substance, the pressure sensitive adhesive layer containing heat generative gel comprising a polyhydric alcohol and a polymer soluble or swellable in the polyhydric alcohol. The literature mentions that the heat generative gel may contain *capsicum* and l-menthol.

Apart from warming devices, it is known that a medicated composition for external use, such as an external preparation or a patch, may contain a warming sensate component having a 4-hydroxy-3-methoxyphenyl group and a warming sensate component having a vanillylamide group, such as capsaicin (see patent literature 3 below).

CITATION LIST

Patent Literature

Patent literature 1: JP 2007-136053A
Patent literature 2: JP 2003-210509A.
Patent literature 3: JP 2003-250829A Unfortunately, the conventional warming devices leave room to study on the technique of prolonging the duration of the warming effect of capsaicin and the technique of reducing the time required for the onset of the warming effect of capsaicin. Development of further advanced techniques is desired.

SUMMARY OF THE INVENTION

The present invention relates to a steam-generative warming device having a steam generating element that releases steam in association with heat generation by the oxidation of an oxidizable metal. The steam generative warming device contains a capsaicin analog and a menthol in a mass ratio, capsaicin analog/menthol, of 1/300 to 1/20000.

To solve the problem, the present inventors have conducted extensive investigations and found as a result that, when a capsaicin or an analog thereof (hereinafter inclusively referred to as a capsaicin analog) is combined with an excess (relative to the capsaicin analog) of a menthol and moist heat in a specific ratio, not only is there obtained a moderate warming effect with a reduced sensation of irritation inherent to the capsaicin analog but, surprisingly, the duration of the moderate warming effect is improved, and the time from the start of the heat generation of the steam-generative warming device until the onset of a warming sensation is reduced.

Based on the findings the present invention provides a steam-generative warming device having a steam generating element that releases steam in association with heat generation by the oxidation of an oxidizable metal. The steam generative warming device contains a capsaicin analog and a menthol in a mass ratio, capsaicin analog/menthol, of 1/300 to 1/20000.

The invention provides a steam generative warming device that provides a long-lasting moderate warming effect and a reduced time from application to a body until the onset of warming sensation. The invention also provides an advantage that such an effect as skin temperature elevation or pain relief is produced in not only the part of a user's body to which the steam generative warming device is applied but in other parts of the body as well.

The invention relates to a steam generative warming device that accomplishes improvements in warming effect and sensation over the above discussed conventional warming devices.

The invention will be described with reference to its preferred embodiments. The steam generative warming device of the invention is designed to be attached to the body of a user to impart heat accompanied by steam, namely moist heat, to the user's body. To achieve this, the steam generative warming device of the invention has a steam generating element. The steam generating element contains an oxidizable metal and water and is configured to release steam in association with heat generation by oxidation of the oxidizable metal.

One of the characteristics of the steam generative warming device resides in the combined use of a capsaicin analog, a menthol, steam, and heat. As defined above, the term "capsaicin analog" as used herein refers to capsaicin or an analog thereof and more concretely a compound represented by general formula (1). Examples of the capsaicin analog include capsaicin, dihydrocapsaicin, nordihydrocapsaicin, homodihydrocapsaicin, homocapsaicin, bishomocapsaicin, trishomocapsaicin, nornorcapsaicin, norcapsaicin, capsaicinol, nonylic acid vanillylamide, and decylic acid vanillylamide, all of which are known capable of imparting a warming sensation to a user. Particularly preferred of these capsaicin analogs are capsaicin and dihydrocapsaicin. The inventors discovered that a combined use of a capsaicin analog as a warming sensate component with an excessive amount (relative to the capsaicin analog) of a menthol achieves not only development of a moderate warming effect but, surprisingly, reduction in time from application to a body part until, the onset of the warming effect and prolongation of the duration of the moderate warming effect.

The inventors also found that the combination of a capsaicin analog and an excessive amount of a menthol is additionally effective in increasing the skin temperature or alleviating the pain in not only the user's body part where the heat generative warming device is applied but other parts of the body as well. Examples of the menthol include l-menthol and dl-menthol, with l-menthol being preferred. Two or more capsaicin analogs may be used in combination. Similarly, two or more menthols may be used in combination.

[Chem. 1]

(1)

wherein R is a C7-C12 alkyl or alkenyl group.

To ensure the above described effects, the mass ratio of a capsaicin analog to a menthol, capsaicin analog/menthol, in the steam generative warming device of the invention is limited to the range of from 1/300 to 1/20000. As long as the capsaicin analog/menthol ratio falls within that range, the stimulation of the highly volatile menthol and the moist heat exert favorable action on the warming effect of the capsaicin analog, resulting in a rapid onset of a warming sensation and a prolonged duration of a moderate warming effect. In this regard, the capsaicin analog/menthol mass ratio is preferably 1/500 to 1/15000, more preferably 1/1000 to 1/7000.

The capsaicin analog and the menthol may be present in the steam generative warming device of the invention either as a mixture or separately in different portions. The latter mode of existence is very favorable in order to make the above described effects pronounced and from the standpoint of storage stability. It is preferred for the capsaicin analog to be present in a portion where it is allowed to migrate to the user's skin during direct contact with the skin, for example in an element of the elements of the steam generative warming device of the invention that is to be brought into direct contact with the user's skin. It is preferred for the menthol, on the other hand, to be present in an element of the elements of the steam generative warming device which does not come into direct contact with the user's skin. Since the steam generative warming device of the invention generates steam, the menthol even when located away from the user's skin accompanies the flow of steam on vaporization and successfully reaches the skin. It is particularly preferred for the menthol to be present in the steam generating element (hereinafter also referred to as a heat generating element) for the reason described later.

In one embodiment, the invention is directed to a steam-generative warming device comprising a steam generating element containing an oxidizable metal and releasing steam in association with heat generation accompanying the oxidation of the oxidizable metal, the steam-generative warming device containing a capsaicin analog and a menthol in a capsaicin analog/menthol mass ratio of 1/300 to 1/20000. In some embodiments, this steam-generative warming device has a first element adapted to be brought into direct contact with the skin of a user and a second element adapted not to be brought into contact with the user's skin, wherein the capsaicin analog is present in the first element adapted to be brought into direct contact with the skin of a user, and the menthol is present in the second element adapted not to be brought into contact with the user's skin.

Figures 1A, 1B:
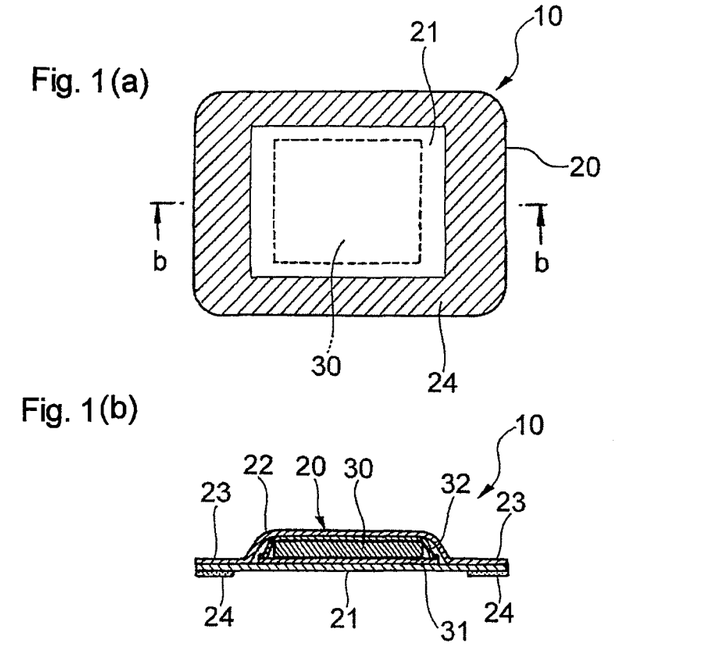
FIG. 1(a) is a plan of an embodiment of the steam generative warming device of the invention, seen from the side of its body side sheet.
FIG. 1(b) is a cross-section taken along line b-b in FIG. 1(a).

FIG. 1 shows one embodiment of the steam generative warming device of the invention. The steam generative warming device 10 of FIG. 1 has a flat shape and includes a bag 20 and a heat generating element 30 enclosed in the bag 20. The bag 20 defines the outer contour of the steam generative warming device 10 and has a flat shape. The bag 20 has a skin facing side that is adapted to face the user's skin while in use and an outer side that is to face outward while in use. The skin facing side of the bag 20 is formed of a body side sheet 21, and the outer side is formed of an outer side sheet 22. The body side sheet 21 and the outer side sheet 22 are substantially equal in shape and are bonded to each other in their peripheral portions 23 by a prescribed means.

The heat generating element 30 is covered with sheeting having air permeability in at least a part thereof. In detail, the heat generating element 30 is covered with a first sheet 31 and a second sheet 32, the first sheet 31 and the second sheet 32 facing the user's skin and outward, respectively, while the steam generative warming device 10 is in use. At least one of the first sheet 31 and/or the second sheet 32 has air permeability in at least a part thereof. The first sheet 31 and the second sheet 32 are substantially equal in shape and are bonded to each other in their peripheral portions (not shown) by a prescribed means. The heat generating element 30 contains an oxidizable metal. The oxidizable metal is oxidized on contact with oxygen coming through the air permeable part of the sheet 31 and/or the sheet 32, thereby to generate heat. The first sheet 31 and the second sheet 32 have properly controlled air permeance so that steam may be released preferentially through the first sheet 31. More specifically, the second sheet 32 has a higher air permeance than the first sheet 31. The term "air permeance" as used herein is a value measured in accordance with JIS P8117, which is defined to be the time required for 100 ml of air to pass through an area of 6.42 cm$^2$ under a given pressure. A higher air permeance means more time needed for air passage, i.e., lower air permeability. Conversely, a lower air permeance means higher air permeability. Air permeance as defined above and air permeability are in a converse relation. The air permeability of the first sheet 31 is equal to or higher than that of the second sheet 32. More specifically, the air permeance of the first sheet 31 is preferably 100 to 30000 s/100 ml, more preferably 500 to 20000 s/100 ml, even more preferably 1000 to 10000 s/100 ml. The second sheet 32 may be air permeable or impermeable. When in using an air permeable sheet as the second sheet 32, the air permeance of the second sheet 32 is equal to or higher than that of the first sheet 31, preferably 8000 to 100000 s/100 ml, more preferably 10000 to 90000 s/100 ml, even more preferably 15000 to 80000 s/100 ml.

The body side sheet 21 forming the bag 20 of the steam generative warming device 10 has a pressure sensitive adhesive 24 on its surface. The pressure sensitive adhesive 24 serves as a means for attaching the steam generative warming device 10 to the user's body. The pressure sensitive adhesive 24 is applied not to overlap the heat generating element 30 in a plan view of the steam generative warming device 10. Specifically, the pressure sensitive adhesive 24 is applied to the peripheral portion of the body side sheet 21 in a pattern surrounding the heat generating element 30 either continuously or discontinuously. The region having the pressure sensitive adhesive 24 applied may be within the peripheral regions of the body side sheet 21 and the outer side sheet 22 where they are bonded together as shown in FIG. 1(b) or may be substantially coincident with the peripheral region where the body side sheet 21 and the outer side sheet 22 are bonded together.

The pressure-sensitive adhesive is preferably such that is capable of maintaining the sheet attached without coming off the skin, particularly such that is able to continue preventing steam from the heat generating element 30 from leaking outside when it is continuously applied to the whole peripheral portion to surround the heat generating element 30. For example, the pressure sensitive adhesive is chosen from known hot melt adhesives based on natural or synthetic rubbers, (meth)acrylic ester resins, silicones, or urethane resins, which are preferably of a non-residue type. The pressure sensitive adhesive may contain additives used in common pressure sensitive adhesives, such as a tackifier, a softener, an inorganic filler, an antioxidant, a UV absorber, and a pigment, as long as the effects of the invention are not impaired.

Of the sheets forming the bag 20 of the steam generative warming device 10, the body side sheet 21 has air permeability and allows for release of steam. The body side sheet 21 may be, for example, a fiber sheet, a porous film, or a perforated film. Considering that the body side sheet 21 is to come into direct contact with the skin of a user, it is preferred for the body side sheet 21 to have an agreeable hand. In this regard, it is preferred that at least a part of the body side sheet 21 be formed of, for example, nonwoven fabric formed of synthetic fiber, such as polyester fiber, polyolefin fiber, polyamide fiber, or polyacrylic fiber, natural fiber, such as cellulose fiber, cotton, wool, or silk, or a mixture thereof by a through-air process, a spun bonding process, a needle punching process, a melt blowing process, a carding method, a thermal bonding method, a hydroentangling method, a solvent bonding method, and the like. In particular, a sheet of nonwoven fabric of hydrophobic fiber, such as polyolefin (e.g., polyethylene or polypropylene) fiber, polyester (e.g., polyethylene terephthalate) fiber, polyamide (e.g., polyamide 6 or polyamide 66) fiber, or polylactic acid fiber, is preferred in that the steam generated from the heat generating element 30 is effectively imparted to the skin thereby to reduce the time for the onset of the warming effect and prolong the duration of the moderate warming sensation. The outer side sheet 22 may or may not have air permeability, which depends on the intended usage of the steam generative warming device 10. The material of the outer side sheet 22 is therefore chosen appropriately according to whether or not air permeability is required.

It is preferred that the body side sheet 21, which is a member contacting the user's skin while the steam generative warming device 10 of FIG. 1 is worn, hold the capsaicin analog on at least its surface contacting the skin. Considering that the capsaicin analog should successfully transfer to the user's skin while the steam generative warming device 10 is worn, the capsaicin analog is preferably present in the region of the body side sheet 21 where the pressure sensitive adhesive 24 is absent, i.e., the central region of the body side sheet 21. In view of producing a moderate warming effect, it is particularly preferred for the capsaicin analog to be present in a region overlapping the heat generating element 30.

A capsaicin analog may be caused to be present on and in the body side sheet 21 by any means selected as appropriate to the material of the body side sheet 21. When the body side sheet 21 is formed, e.g., of nonwoven fabric, a capsaicin analog can successfully be supported by dispersing the capsaicin among the fibers in the course of forming the nonwoven fabric, by applying a liquid composition containing the capsaicin analog to the surface of the nonwoven fabric, or by immersing the nonwoven fabric in the liquid composition. When the body side sheet 21 is partially formed, e.g., of nonwoven fabric, too, the capsaicin analog can successfully be supported by dispersing the capsaicin among the fibers in the course of forming the nonwoven fabric, by applying a liquid composition containing the capsaicin analog to the surface of the nonwoven fabric, or by immersing the nonwoven fabric in the liquid composition.

The amount of a capsaicin analog to be held in/on the body side sheet 21 is preferably 0.05 to 5.0 $\mu g/cm^2$, more preferably 0.08 to 3.0 $\mu g/cm^2$, based on the area of the region having the capsaicin analog applied, in view of obtaining a favorable intensity of a capsaicin analog-induced warm feeling.

As previously stated, the menthol may be held in the body side sheet 21 similarly to the capsaicin analog or in any other member, for example, the heat generating element 30, the sheet 31, the sheet 32, or the outer side sheet 22. The menthol is preferably present in the heat generating element 30, taking into consideration the stability of the menthol during storage and ease of incorporating the menthol therein.

The amount of the menthol to be incorporated in the steam generative warming device 10 is such that satisfies the above specified capsaicin analog to menthol mass ratio, preferably ranging from 0.05 to 10 $mg/cm^2$, more preferably from 0.1 to 5.0 $mg/cm^2$. When the menthol is present in the heat generating element 30, the ratio of the menthol to the heat generating element 30 is preferably 0.02% to 5.0% by mass, more preferably 0.04% to 2.5% by mass.

When a menthol is incorporated into the heat generating element 30, it is preferred that the menthol be supplied to the heat generating element 30 together with a dissolving agent. In particular, a menthol is uniformly distributed throughout the heat generating element 30 by adding a solution of the menthol in the dissolving agent to the heat generating element 30. Because a menthol is generally an oily substance, the dissolving agent is preferably an organic solvent capable of dissolving an oily substance and harmless to the human body. Because the heat generating element 30 contains water to induce a heat generative chemical reaction, the dissolving agent is preferably an organic solvent having good compatibility with water. Using a dissolving agent having good water compatibility allows for uniform distribution of the dissolving agent throughout the heat generating element 30. Examples of such an organic solvent include alcohols which are liquid at 25° C., such as polyhydric alcohols, e.g., ethylene glycol, propylene glycol, dipropylene glycol, 1,3-butylene glycol, glycerol, polyethylene glycol (e.g., polyethylene glycol 200 or polyethylene glycol 400), polypropylene glycol, and 1,3-propanediol, and lower alcohols, e.g., ethanol. Preferred of them are polyhydric alcohols which are liquid at 25° C., for they release a large quantity of menthol. Since the invention involves heat generation due to a chemical reaction, the dissolving agent to be used is preferably non-smelling during use. Particularly preferred are polyethylene glycol and propylene glycol in terms of effective enhancement of menthol release.

The dissolving agents may be used either individually or in combination of two or more thereof. In order that a menthol be sufficiently dissolved and distributed uniformly throughout the heat generating element 30 while minimizing adverse influences on heat generation characteristics, the dissolving agent is preferably used in a concentration of 0.01% to 20%, more preferably 0.1% to 10%, even more preferably 0.5% to 5%, by mass based on the total weight of the heat generating element 30. In order for a menthol to be dissolved sufficiently, the amount of the dissolving agent is preferably 5% to 99%, more preferably 10% to 93%, even more preferably 30% to 90%, even more preferably 50% to 80%, by mass based on the sum of the dissolving agent and the menthol.

Incorporating a menthol into the heat generating element 30 can be achieved by, for example, preparing a solution of the menthol in a dissolving agent and adding the solution to a separately prepared heat generating element 30 by spraying, coating, dipping or a like method.

Another method for incorporating a menthol into the heat generating element 30, which is also a preferred method, includes adding a menthol to the heat generating element 30 together with a dissolving agent and a surfactant. In this method, a combined use of a first dissolving agent (A) and a second dissolving agent (B) as described below allows for marked improvement on menthol releasability from the heat generating element 30.

(A) A first dissolving agent containing at least one oil which is liquid at 25° C. selected from the group consisting of a hydrocarbon oil, an ester oil, a monohydric alcohol, a fatty acid, a silicone oil, a glyceride, and a vegetable oil.

(B) A second dissolving agent containing a polyhydric alcohol.

Examples of the first dissolving agent include hydrocarbon oils, such as liquid paraffin and squalene; ester oils, such as isopropyl myristate, isopropyl palmitate, cetyl 2-ethylhexanoate, octyldodecyl myristate, and neopentyl glycol dicaprate; monohydric alcohols, such as 2-hexyldecanol, 2-octyldodecanol, 2-decyltetradecanol, and isostearyl alcohol; fatty acids, such as isostearic acid and oleic acid; cyclic or linear silicone oils, such as dimethylpolysiloxane, methylphenylpolysiloxane, and cyclomethicone; monoglycerides, such as dioleyl diglyceride; diglycerides, such as diethylhexyl monoglyceride; triglycerides, such as caprylic triglyceride, and caprylic/capric triglyceride; and vegetable oils, such as jojoba oil, macadamia nut oil, olive oil, and castor oil. Preferred dissolving agents among them are monohydric higher alcohols having 16 to 22 carbon atoms; for they have higher compatibility with menthols and are capable of uniformly distributing a smaller amount of menthol in the heat generating element 30. This is advantageous for lessening the influences on heat generation and causing no perceptible unusual smell during heat generation.

To secure a sufficient heat value, it is preferred for the first dissolving agent to be present in the heat generating element 30 in an amount of 0.01% to 5%, more preferably 0.05% to 3%, even more preferably 0.1 to 1%, by mass. The mass ratio of the first dissolving agent to the menthol, first dissolving agent/menthol, is preferably 0.01 to 2.0, more preferably 0.05 to 1.0, even more preferably 0.1 to 0.5.

Examples of the polyhydric alcohols used as the second dissolving agent include ethylene glycol, propylene glycol, dipropylene glycol, 1,3-butylene glycol, glycerol, polyethylene glycol (e.g., polyethylene glycol 200 or polyethylene glycol 400), polypropylene glycol, and 1,3-propanediol. Preferred of them is polyethylene glycol; for it effectively increases the releasability of the menthol while maintaining the emulsifying and dispersing effect of a surfactant on the menthol.

To secure a sufficient heat value and to improve menthol releasability from the heat generating element 30, it is preferred for the second dissolving agent to be present in the heat generating element 30 in an amount of 0.01% to 5%, more preferably 0.05% to 3%, even more preferably 0.1 to 2%, by mass. The mass ratio of the second dissolving agent to the menthol, second dissolving agent/menthol, is preferably 0.1 to 5, more preferably 0.5 to 3, even more preferably 1 to 2. By using the second dissolving agent and the menthol in that ratio, good release of the menthol by the heat of the heat generating element 30 is achieved while minimizing inhibition of heat generation.

The combination of dissolving agents is selected with considerations given to the compatibility with the menthol and water and the influence on the affinity between the surfactant and water. Specifically, a preferred combination of the first and the second dissolving agent is a combination of a monohydric higher alcohol as the first dissolving agent and a polyhydric alcohol as the second dissolving agent. Using this combination allows more successful emulsification of the menthol and water in the heat generating element 30 so as to minimize inhibition of heat generation and accomplish good release of the menthol during heat generation. A particularly preferred first dissolving agent is 2-octyldodecanol or 2-hexyldecanol. A particularly preferred second dissolving agent is polyethylene glycol, especially polyethylene glycol with a molecular weight of 200 to 600.

As the surfactant for use in combination with a menthol and the above described dissolving agent, any of cationic surfactants, anionic surfactants, nonionic surfactants, and amphoteric surfactants may be used as long as it is acceptable in cosmetics, pharmaceuticals, and so on. Nonionic surfactants are particularly advantageous in that they allow successful emulsification of an aqueous electrolyte contained in the heat generating element 30 and a menthol, exhibit high emulsion stability, permit good release of a menthol with heat generation by the heat generating element 30, and can cause little hindrance to heat generation of the heat generating element 30.

Suitable nonionic surfactants include polyoxyethylene alkyl ethers, polyoxyethylene hydrogenated castor oil, polyoxyethylene alkyl allyl ethers, sorbitan fatty acid esters, polyoxyethylene sorbitan fatty acid esters, polyoxyethylene sorbitol fatty acid esters, fatty acid monoglycerides, polyoxyethylene fatty acid esters, polyoxyethylene alkylamines, alkylalkanolamides, sucrose fatty acid esters, polyglycerol fatty acid esters, polyoxyethylene fatty acid glycerides, and polyoxyethylene-polyoxypropylene copolymers. Preferred of them are polyoxyethylene surfactants, such as polyoxyethylene alkyl ethers, polyoxyethylene hydrogenated castor oil, polyoxyethylene alkyl allyl ethers, polyoxyethylene sorbitan fatty acid esters, polyoxyethylene sorbitol fatty acid esters, polyoxyethylene fatty acid esters, polyoxyethylene alkylamines, polyoxyethylene fatty acid glycerides, and polyoxyethylene-polyoxypropylene copolymers. More preferred are polyoxyethylene hydrogenated castor oil, polyoxyethylene alkyl ethers, and the like; for they exert an interaction with the second dissolving agent to improve their affinity to water. Even more preferred is polyoxyethylene hydrogenated castor oil or a polyoxyethylene alkyl ether, particularly polyoxyethylene hydrogenated castor oil, each having an HLB of 10 to 20, more preferably 12 to 18, even more preferably 13 to 17. The HLB value as referred to herein is a value obtained by the equation of Griffin (J. Soc. Cosmet. Chem., 1, 311 (1949)).

The surfactant content in the heat generating element 30 is preferably 0.01% to 5%, more preferably 0.05% to 3%, even more preferably 0.1% to 2%, by mass. With this surfactant content, dispersibility of the menthol and the dissolving agent(s) in the heat generating element 30 is further improved, allowing for more uniform distribution of the menthol in the heat generating element 30. As a result, the menthol is better released by the heat generated by the heat generating element 30, and the influence on heat generation is minimized. The amount of the surfactant relative to the second dissolving agent is preferably such that the mass ratio of the second dissolving agent to the surfactant is 0.1 to 5, more preferably 0.5 to 2. With the amount of the surfactant failing in that range, hindrance to the heat generation of the heat generating element 30 is further minimized, the emulsification stability of the menthol in water present in the heat generating element 30 is further improved, and the menthol is still better released.

As previously noted, the steam generative warming device 10 of the present embodiment has a pressure sensitive adhesive 24 applied to form a pressure sensitive adhesive layer in the peripheral region located outside the central region of the body side sheet 21. In the case where the pressure sensitive adhesive layer is continuous to surround the central region, the central region of the body side sheet 21 will be enclosed by the peripheral pressure sensitive adhesive layer when the steam generative warming device 10 is attached to the skin of a user. That is, there is defined a sealed portion by the user's skin, the central region of the body side sheet 21, and the pressure sensitive adhesive layer on the peripheral region. Upon heat generation, the sealed portion will be filled with steam generated from the heat generating portion 30 and also with vapor of the menthol, and the capsaicin analog will transfer from the central region of the body side sheet 21 to the skin by direct contact. As a result, the above discussed effects will become more pronounced, that is, the duration of a moderate warming effect is extended, and the rise time needed until the warming sensation is perceived is reduced.

In order to further ensure the effects of the capsaicin analog in improving the rise time of the warming effect and the duration of a moderate warming effect, it is also important for the steam generative warming device 10 to generate a sufficient amount of steam. From this viewpoint, it is preferred that the amount of steam generated and given to the skin per unit area per 60 minutes over a period of 5 hours from the time of applying to the wearer be 5 to 50 mg/(cm$^2$·60 min), more preferably 6 to 40 mg/(cm$^2$·60 min), even more preferably 8 to 35 mg/(cm$^2$·60 min).

The amount of steam generated is measured, for example, as follows. A tester having a 4.2-liter closed chamber adjusted to 1% RH or less in which 2.1 l/min of dry air is fed is provided. A steam generative warming device 10 of prescribed size is placed in the chamber and let to heat up so that water vapor generated may spread in the chamber. The humidity of the air discharged from the chamber is measured with a hygrometer, from which the amount of water vapor generated per unit time after the start of heat generation is calculated according to equation (1) shown below. The cumulative amount of water vapor generated over a period of 60 minutes is obtained and converted to a value per unit area. In the following equations, e stands for water vapor pressure (Pa); es, a saturated water vapor pressure (Pa; according to JIS Z8806); T, temperature (° C.; dry-bulb temperature); and s, sampling cycle (sec).

Relative humidity $U(\% \text{ RH}) = (e/es) \times 100$

Absolute humidity $D(g/m^3) = (0.794 \times 10^{-2} \times e)/(1 + 0.00366T) = (0.794 \times 10^{-2} \times U \times es)/[100 \times (1 + 0.00366T)]$ Unit air volume $P(\text{liter}) = (2.1 \times s)/60$ Amount of water vapor per unit time $A(g) = (P \times D)/1000$ (1)

The term "amount of water vapor" as used herein denotes the amount of water vapor (steam) having reached the skin through the first sheet 31 and the body side sheet 21 located outward of the first sheet 31. When the first sheet 31 and the second sheet 32 are different in air permeability, the amount of steam generated and imparted to the skin is re-calculated taking the air permeance ratio of the two sheets into consideration.

Generation of steam in the above recited range of amount is achieved by, for example, appropriately adjusting the air permeance (JIS P8117) of the first sheet 31 and the second sheet 32 that cover the heat generating element 30. For example, steam is allowed to be released outside preferentially through the first sheet 31 by increasing the air permeance of the second sheet over that of the first sheet 31 disposed on the user's body side.

In order to further ensure the effects of the capsaicin analog in improving the rise time of the warming effect and the duration of a moderate warming effect, it is advantageous that the steam generative warming device 10 reaches an adequately elevated temperature as well as generates a sufficient amount of steam. From this viewpoint, it is preferred for the steam generative warming device 10 to have heat generation characteristics such that the temperature of the surface of the user's skin to which it is applied directly may be kept at 38° to 43° C. for 1 to 5 hours. The skin surface temperature is measured at a position right under the heat generating element of the steam generative warming device 10 attached to the body of a test subject (e.g., the back of the neck or the shoulder). The skin surface temperature (right under the heat generating element) is measured with a body thermometer Coretemp CM-210 equipped with a skin temperature probe PDK161, both from Terumo Corp.

The steam generative warming device 10 satisfying the above described demands for the amount of steam and the heat generation temperature may be obtained mainly by controlling the contents of the oxidizable metal and water in the heat generating element 30 and the air permeance of the sheet 31 covering the heat generating element 30.

The oxidizable metal used in the heat generating element 30 may be the same as those commonly used in the art, typically including iron powder. The heat generating element 30 is made up of appropriately selected components according to its structure. For example, the heat generating element 30 may be a heat generating sheet obtained by preparing a molded sheet containing, for example, an oxidizable metal and a reaction accelerator and adding an electrolyte solution containing an electrolyte and water to the molded sheet. The heat generating element 30 may be heat generative powder made up of an oxidizable metal, a reaction accelerator, an electrolyte, and water. The contents of the electrolyte and water are preferably such that the amount of the aqueous electrolyte solution having an electrolyte concentration of 0.3% to 10%, more preferably 0.5% to 7%, by weight is from 20 to 80 parts by weight per 100 parts by weight of the molded sheet or powder containing the oxidizable metal, the reaction accelerator, and so on.

Figure 2:
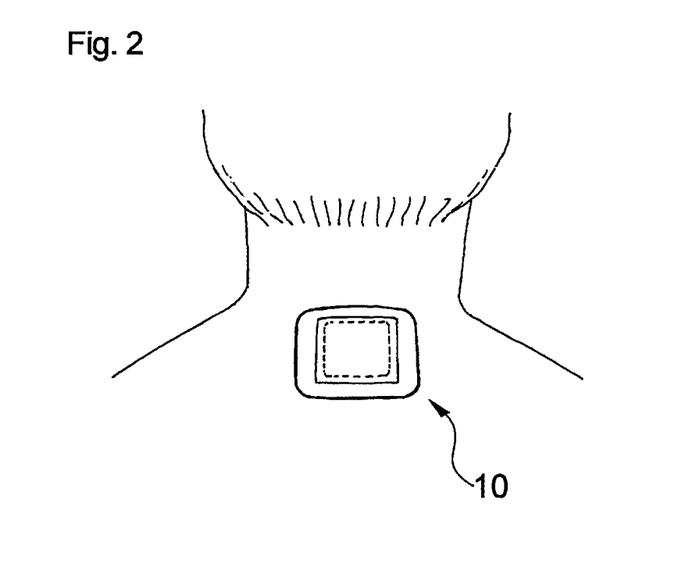
FIG. 2 shows a usage of the steam generative warming device shown in FIGS. 1(a) and 1(b).

The steam generative warming device 10 of the present embodiment is used as directly attached to the user's skin as shown in FIG. 2. Having a higher rate of rise of the warming effect and a longer duration of the moderate warming effect than conventional warming devices, the steam generative warming device 10 is capable of local warming at a smaller size than in the case of conventional warming devices. The warming device 10 of a smaller size has a so decreased oxidizable, metal content and is likely to have a smaller total heat value than a larger one and can therefore fail to impart a warming sensation for a sufficient duration of time. Nonetheless, the combined use of a capsaicin analog and a menthol achieves a great advantage of enabling such a small warming device to impart a long-lasting moderate warming sensation. From this point of view, the characteristics of the warming device 10 of the present embodiment are pronouncedly exhibited to great advantage particularly when designed to have a small heat generating element 30 in a plan, preferably when the heat generating element 30 has a plan view area of 1.0 to 30 $cm^2$, more preferably 2.0 to 20 $cm^2$.

While the invention has been described chiefly based on its preferred embodiment, the invention is not limited thereto, and various changes and modifications can be made therein. For instance, the steam generative warming device 10 is not limited to the shape shown in FIG. 1 and may have various shapes, such as a circle, an ellipse, a polygon other than a rectangle, and a combination thereof. The part of body to which the steam generative warming device 10 is applied is not limited to the part shown in FIG. 2 and may be applied to various body parts.

EXAMPLES

The invention will now be illustrated greater detail by way of Examples, but it should be noted that the invention is not limited thereto. Unless otherwise noted, all the percents and parts are by mass.

Example 1

A steam generative warming device 10 shown in FIG. 2 was made according to the following procedure.
(1) Making of Heat Generating Element 30 of Sheet Form
Composition of Raw Materials:
Oxidizable metal: iron powder RKH (trade name) from Dowa Iron Powder Co., Ltd. 83%
Fibrous material: pulp fiber NBKP Mackenzie (trade name) from Fletcher Challenge Canada, Ltd. (CSF: adjusted to 200 ml) 8%
Reaction accelerator: activated carbon Carboraffin (trade name) from Japan EnviroChemicals, Ltd. (average particle size: 45 μm) 9%
To the mixture of raw materials listed above were added 0.7 parts of a polyamide-epichlorohydrin resin WS4020 (trade name) from Seiko PMC Corp. as a cationic flocculant and 0.18 parts of sodium carboxymethyl cellulose HE1500F (trade name) from Dai-ichi Kogyo Seiyaku Co., Ltd. as an anionic flocculant per 100 parts of the solid contents of the mixture (the total of the oxidizable metal, fibrous material, and activated carbon). The mixture was then suspended in industrial water to a solids concentration of 12%.
Papermaking Conditions:
The slurry thus prepared was diluted with water to 0.3% in front of the head box and drained on an inclined short-wire paper machine at a line speed of 15 in/min to form a wet mat.
Drying Conditions:
The wet mat was dewatered under pressure between felt blankets, and was passed as such between 140° C. heated rollers to be dried to a water content of 5% or less. The dried sheet had a basis weight of 450 $g/m^2$ and a thickness of 0.45 mm. As a result of measurement with a thermogravimetric analyzer TG/DTA 6200 from Seiko Instruments Inc., the resulting molded sheet was found to be made up of 83% iron, 9% activated carbon, and 8% pulp.
Making of heat generating element 30 of sheet form:

The resulting molded sheet was cut to measure 25 mm by 25 mm. Four cut sheets were stacked one on top of another, and 40 parts of a menthol-containing electrolyte solution having the composition shown in Table 1 below per 100 parts of the stack was syringed into the stack. The amounts of the menthol, 2-octyldodecanol, polyethylene glycol 400, and polyoxyethylene hydrogenated castor oil (60 E.O.) (HLB: 14.0) were 0.9%, 0.2%, 1.4%, and 0.9%, respectively, relative to the total mass of the heat generating element 30. The electrolyte solution was allowed to impregnate throughout the stack by capillarity to provide a heat generating element 30 of rectangular sheet form measuring 25 mm by 25 mm. The menthol content of the heat generating element 30 was 2.18 $mg/cm^2$. The heat generating element 30 was covered with two air-permeable polyethylene films different in air permeance. The air permeance (JIS P8117) of the air permeable film 31 used on the skin facing side was 2500 s/100 ml, while that of the air permeable film 32 used on the outer side was 30000 s/100 ml.

TABLE 1

|  | Composition (mass %) |
| --- | --- |
| 1-Menthol | 3.0% |
| Polyethylene glycol 400 | 4.4% |
| 2-Octyldodecanol | 0.7% |
| Polyoxyethylene hydrogenated castor oil (60 E.O.; HLB: 14.0) | 3.0% |
| Sodium chloride | 4.4% |
| Purified water | balance |
| Total | 100.0% |

(2) Making of Steam Generative Warming Device 10
The heat generating element 30 covered with the air permeable polyethylene films 31 and 32 was put in a bag 20 formed of a needle-punched nonwoven fabric of polyethylene terephthalate having a basis weight of 40 $g/m^2$ as a body side sheet 21 and a polypropylene nonwoven fabric having a basis weight of 50 $g/m^2$ as an outer side sheet 22. A hot pepper tincture containing 0.032 g/100 ml of a capsaicin analog (capsaicin, dihydrocapsaicin, etc.) was uniformly dispersed in ethanol, a volatile solvent, and the resulting solution was applied to the central region of the body side sheet 21 (nonwoven fabric) and dried to be held therein. The area where the capsaicin analog is held was 7.5 $cm^2$, and the amount of the capsaicin analog held was 0.54 $\mu g/cm^2$. An SIS copolymer-based hot-melt pressure-sensitive adhesive was continuously applied to the peripheral region of the body side sheet 21 over an area of 15 $cm^2$. There was thus made a desired steam generative warming device 10.

Example 2

A steam generative warming device 10 was made in the same manner as in Example 1, except for changing the amount of the menthol held to 0.24 $mg/cm^2$.

Example 3

A steam generative warming device 10 was made in the same manner as in Example 1, except for changing the amount of the menthol held to 0.53 $mg/cm^2$.

Example 4

A steam generative warming device 10 was made in the same manner as in Example 1, except for changing the amount of the menthol held to 3.90 $mg/cm^2$.

Example 5

A steam generative warming device 10 was made in the same manner as in Example 1, except that the menthol was held in the body side sheet 21 similarly to the capsaicin analog.

Example 6

A steam generative warming device 10 was made in the same manner as in Example 1, except for changing the amount of the capsaicin held to 1.3 µg/cm².

Example 7

A steam generative warming device 10 was made in the same manner as in Example 1, except for changing the amount of the capsaicin held to 0.13 µg/cm².

Example 8

A steam generative warming device 10 was made in the same manner as in Example 1, except for changing the air permeance of the first sheet 31 and the second sheet 32 both to 10000 s/ml 10000 s/100 ml and 10000 s/ml 10000 s/100 ml so that the amount of steam generated might be changed to 7.3 mg/(cm2·60 min).

Comparative Example 1

Comparative Example 1 presents an example of a dry heat generative warming device. A dry heat generative warming device was made in the same manner as in Example 1, except that the heat generating element 30 was prepared by adding to 100 parts of the molded sheet 40 parts of a 5.0% aqueous solution of sodium chloride as an electrolyte.

Comparative Example 2

Comparative Example 2 presents an example where no menthol was used. A steam generative warming device was made in the same manner as in Example 1, except for using no menthol.

Comparative Example 3

Comparative Example 3 presents an example where a menthol was used, in extra large excess relative to the capsaicin. A steam generative warming device was made in the same manner as in Example 1, except for using menthol in extra large excess.
Evaluation The warming devices obtained in Examples and Comparative Examples were evaluated for the quickness of the onset of a warming sensation, duration of a moderate warming sensation, and intensity of skin stimulation by the following test methods. The amount of steam generated and the skin surface temperature were measured by the methods described above. The results obtained are shown in Table 2 below.

(1) Quickness of Onset of Warming Sensation

Quickness of the onset of a warming sensation was evaluated by three expert panel members as follows. Each of the steam generative warming devices and the dry warming device of Examples and Comparative Examples was applied to a shoulder of each panel member for 3 hours. Changes in warming sensation felt by the panel members were recorded, the warming sensation being graded 0: no warming sensation; 1: a faint warming sensation; 2: a slightly faint warming sensation; 3: a moderate warming sensation; 4: a slightly strong warming sensation; or 5: a strong warming sensation. The time needed for the warming device to make the wearer feel warmed to grade 1 (a faint warming sensation) from the time of application was measured, and the results were averaged over the three panel members.

(2) Duration of Moderate Warming Sensation (Warming Effect Duration)

Duration of a moderate warming sensation was evaluated by three expert panel members. Each of the steam generative warming devices and the dry warming device of Examples and Comparative Examples was applied to a shoulder of each panel member for 3 hours. Changes in warming sensation felt by the panel members were recorded, the warming sensation being graded 0: no warming sensation; 1: a faint warming sensation; 2: a slightly faint warming sensation; 3: a moderate warming sensation; 4: a slightly strong warming sensation; or 5: a strong warming sensation. The period from the time when the warming sensation was graded 2 (slightly faint) until the end of the duration during which the warming sensation was graded 4 (slightly strong) was measured. The results obtained were averaged over the three panel members.

(3) Intensity of Skin Stimulation

The intensity of skin stimulation was evaluated by three expert panel members as follows. Each of the steam generative warming devices and the dry warming device of Examples and Comparative Examples was applied to a shoulder of each panel member for 3 hours. The intensity of skin stimulation was scored in five grades, 0: no stimulation; 1: weak or too weak stimulation; 2: slightly weak stimulation; 3: moderate stimulation; 4: slightly strong stimulation; 5: strong or too strong stimulation. The scores by the panel members were averaged,

TABLE 2

| | Example | | | | | | | | Comparative Example | | |
|---|---|---|---|---|---|---|---|---|---|---|---|
| | 1 | 2 | 3 | 4 | 5 | 6 | 7 | 8 | 1 | 2 | 3 |
| Capsaicin Analog (µg/cm²) | 0.54 | 0.54 | 0.54 | 0.54 | 0.54 | 1.3 | 0.13 | 0.54 | 0.54 | 0.54 | 0.13 |
| Menthol (mg/cm²) | 2.18 | 0.24 | 0.53 | 3.90 | 2.18 | 2.18 | 2.18 | 2.18 | 2.18 | 0 | 5.31 |
| Capsaicin Analog/Menthol | 1/4035 | 1/451 | 1/981 | 1/7231 | 1/4035 | 1/1676 | 1/16760 | 1/4035 | 1/4035 | — | 1/40846 |
| Steam Generation | yes | yes | yes | yes | yes | yes | yes | yes but less | no | yes | yes |
| Location of Capsaicin Analog | body side sheet | body side sheet | body side sheet | body side sheet | body side sheet | body side sheet | body side sheet | body side sheet | body side sheet | body side sheet | body side sheet |
| Location of Men- | heat | heat | heat | heat | heat | heat | heat | heat | heat | — | heat |

TABLE 2-continued

|  | Example | | | | | | | | Comparative Example | | |
| --- | --- | --- | --- | --- | --- | --- | --- | --- | --- | --- | --- |
|  | 1 | 2 | 3 | 4 | 5 | 6 | 7 | 8 | 1 | 2 | 3 |
| thol | generating element | generating element | generating element | generating element | generating element | generating element | generating element | generating element | generating element |  | generating element |
| Quickness of Onset of Warming Sensation (time required to reach grade 1) (min) | 7.5 | 11.7 | 8.8 | 7.5 | 9.2 | 4.2 | 11.7 | 12.5 | — | 17.5 | 25.0 |
| Warming Effect Duration (grades 2 to 4) (min) | 90.0 | 97.5 | 95.0 | 66.3 | 65.0 | 93.3 | 56.3 | 70.0 | 0.0 | 100.0 | 3.3 |
| Intensity of Skin Stimulation (in grades 0 to 5) | 3.0 | 3.7 | 4.0 | 3.0 | 2.7 | 4.3 | 2.3 | 2.0 | 0.3 | 5.0 | 1.3 |
| Amount of Steam Generated (mg/(cm$^2$ · 60 min)) | 20.9 | 20.9 | 20.9 | 20.9 | 20.9 | 20.9 | 20.9 | 7.3 | 0 | 20.9 | 20.9 |
| Duration of Skin Surface Temperature 38° to 43° C. (hr) | ≥2 | ≥2 | ≥2 | ≥2 | ≥2 | ≥2 | ≥2 | ≥2 | ≥2 | ≥2 | ≥2 |

As is apparent from the results in Table 2, the steam generative warming devices of Examples impart a moderate warming sensation without causing an uncomfortable irritating sensation, rapidly develop a warming sensation, and achieve a long duration of a moderate warming effect. In contrast, the dry warming device that is not accompanied by steam generation (Comparative Example 1) does not impart a sufficient warming sensation. The warming device that does not contain a menthol (Comparative Example 2) imparts a warming sensation but is slow in developing the warming effect and causes strong unpleasant irritation. The warming device containing a very large excess of a menthol (Comparative Example 3) fails to have a long duration of a moderate warming effect.

Figure 3:
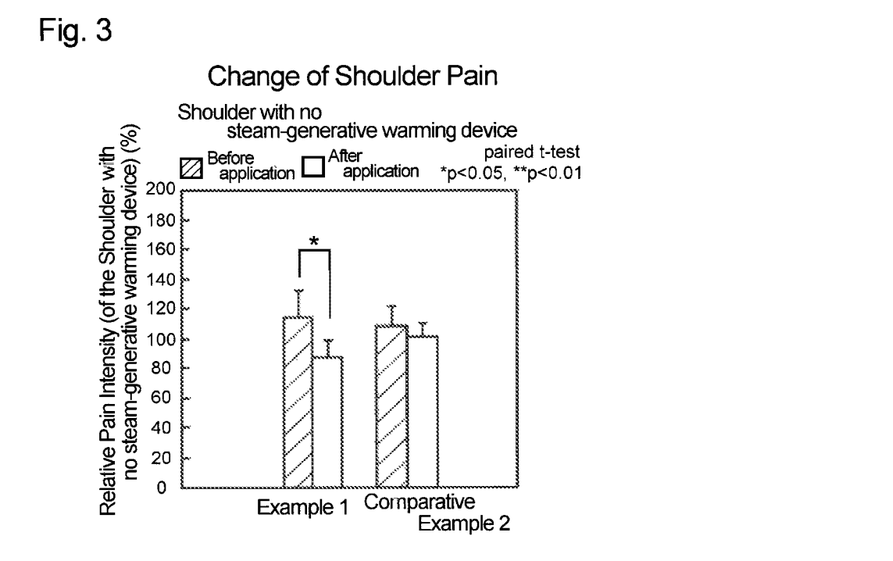
FIG. 3 is a graph representing a change in pain of a shoulder to which the steam generative warming device of Example 1 or Comparative Example 2 is not applied.
Figure 4:
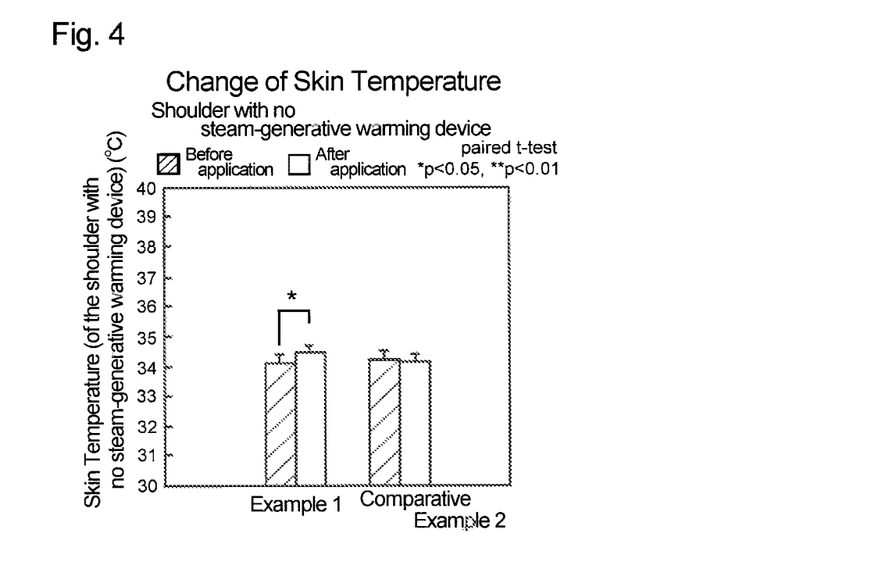
FIG. 4 is a graph showing a change in skin temperature of a shoulder to which the steam generative warming device of Example 1 or Comparative Example 2 is not applied.

The steam generative warming devices of Example 1 and Comparative Example 2 were additionally evaluated for (a) an effect on the change in a shoulder pain and (b) an effect on the change in the skin temperature by the following test methods. The results obtained are shown in FIGS. 3 and 4.

(a) Change in Shoulder Pain

The steam generating warming device was applied to one of the shoulders of 10 test subjects having pain in both shoulders for 3 hours. A change in the level of pain of the other shoulder having no warming device applied before and after application of the warming device to one of the shoulders was evaluated in accordance with the following procedures (1) to (5) using a device for quantitative analysis of perception and pain sensation "Pain Vision PS-2100" from Osachi Co., Ltd. The results obtained are shown in FIG. 3.

(1) Determination of Perception Threshold

The perception threshold of each subject was determined beforehand. Two electrode pads were attached to the inner side of the left forearm with a spacing of 2 cm, and an increasing current was applied thereto. The minimum current at which the subject perceives any stimulation on the inner side of his or her left forearm was taken as a current perception threshold.

(2) Determination of Pain Intensity of Shoulder with No Warming Device (Before Application of Warming Device to the Other Shoulder)

The pain intensity of the subject's shoulder before application of the steam generative warming device was determined as follows. Because a shoulder pain is induced by external stimulation, such as pressing or turning the shoulder, a given pressure (4.5 kg/1.5 mm-diameter) was given to a point of either shoulder where the subject complains of pain with a push pull gauge (Aikoh Engineering Co., Ltd.) to cause pain. Two electrode pads had been attached to the inner side of the left forearm with a spacing of 2 cm, and an increasing current was applied thereto in the same manner as in (1) above. The subject reported the time when the electrical stimulation reached the same intensity of the shoulder pain, and the current at that time was taken as a current corresponding to the pain of shoulder with no warming device (before application of the warming device). The pain intensity, which was taken as "pain intensity of the shoulder with no warming device (before application of warming device)", was calculated using the thus determined current value according to formula (1).

Pain intensity of the shoulder with no warming device (before application of warming device)=
[(current corresponding to pain of shoulder with no warming device (before application of warming device)−current perception threshold)/current perception threshold]×100     (1)

(3) Determination of Pain Intensity of Right Forearm (Before Application of Warming Device)

A given pressure (4.5 kg/15 mm-diameter) was given to the right forearm using a push pull gauge (Aikoh Engineering Co., Ltd.) to cause a pain. Two electrode pads had been attached to the inner side of the left forearm with a spacing of 2 cm, and an increasing current was applied thereto in the same manner as in (1) above. The subject reported the time when the electrical stimulation reached the same level of the right forearm pain, and the current at that time was taken as a current corresponding to pain of the right forearm (before application of warming device). The pain intensity, which was taken as "pain intensity of the right forearm (before application of warming device)", was calculated according to formula (2):

Pain intensity of the right forearm (before application of warming device)=[(current corresponding to pain of right forearm (before application of warming device)−current perception threshold/current perception threshold)]×100  (2)

(4) Determination of Relative Pain Intensity of Shoulder with No Warming Device (Before Application of Warming Device)

The relative pain intensity of the shoulder with no warming device (before application of warming device) was calculated from the pain intensity of the shoulder with no warming device applied (before application of the warming device) as determined in (2) above and the pain intensity of the right forearm (before application of warming device) as determined in (3) above according to formula (3):

Relative pain intensity of the shoulder with no warming device (before application of warming device)=(pain intensity of the shoulder with no warming device (before application of warming device)/pain intensity of the right forearm (before application of warming device))×100  (3)

(5) Determination of Relative Pain Intensity of the Shoulder with No Warming Device (after Application of Warming Device)

The warming device to be tested was applied to one of the shoulders for 3 hours. Thereafter, the same procedures of (2) to (4) described supra were repeated to determine the pain intensity of the other shoulder having no warming device applied (after application of the warming device) and the pain intensity of the right forearm (after application of the warming device). The relative pain intensity of the shoulder with no warming device applied (after application of the warming device) was then calculated.

(b) Change in Skin Temperature

The steam generating warming device was applied to one of the shoulders of 10 test subjects having pain in both shoulders for 3 hours. A change in the skin temperature (the average skin temperature per 3 minutes) of the other shoulder with no warming device applied before and after application of the warming device to one of the shoulders was evaluated using a temperature logger LT-8 from Gram Corp. The results obtained are shown in FIG. 4.

As is apparent from FIG. 3, when the steam generative warming device obtained in Example 1 is applied to one of the subject's shoulders, a significant difference in pain before and after the application is surprisingly observed with the other shoulder to which the warming device is not applied in addition to the shoulder applied the warming device. In contrast, when the steam generative warming device of Comparative Example 2 is applied to one of the shoulders, significant improvement in pain alleviation is not observed compared with the other shoulder having no warming device applied although pain alleviation is observed with the shoulder applied the warming device.

As is apparent from FIG. 4, when the steam generative warming device obtained in Example 1 is applied to one of the subject's shoulders, a significant increase in skin temperature before and after the application is surprisingly observed with the other shoulder to which the warming device is not applied. In contrast, when the steam generative warming device of Comparative Example 2 is applied to one of the shoulders, no significant difference (increase) in skin temperature is observed with the other shoulder having no warming device applied.

What is claimed is:

1. A steam-generative warming device comprising
(a) a steam generating element that contains an oxidizable metal configured to release steam in association with heat generation accompanying oxidation of the oxidizable metal,
wherein the steam-generative warming device has a skin facing side configured to face a user's skin while in use, the skin facing side comprising a body side sheet configured to be in direct contact with the user's skin while the device is worn,
the body side sheet comprising a pressure sensitive adhesive applied to the body side sheet in a continuous pattern that surrounds but does not overlap the steam generating element when viewed in a plan view of the steam-generative warming device, the pressure sensitive adhesive forming a continuous pressure sensitive adhesive layer in the body side sheet's peripheral region outside of the body side sheet's central region;
(b) a capsaicin analog, wherein the capsaicin analog is present only (i) in, (ii) on, or (iii) both in and on, the body side sheet's central region where the pressure sensitive adhesive is absent, in an amount of 0.05 to 3.0 µg/cm$^2$, based on the area of the region having the capsaicin analog applied; and
(c) a menthol,
wherein the menthol is held in the steam generating element together with
(A) a first dissolving agent that contains at least one oil that is liquid at 25° C. and is selected from the group consisting of a hydrocarbon oil, an ester oil, a monohydric alcohol, a fatty acid, a silicone oil, a glyceride and a vegetable oil, and
(B) a second dissolving agent that contains a polyhydric alcohol,
wherein the mass ratio of the capsaicin analog to the menthol in the steam-generative warming device is 1/300 to 1/20000.

2. The steam-generative warming device according to claim 1, further comprising a bag in which the steam generating element is enclosed,
the bag having a skin facing side configured to face the skin of a user while in use and an outer side configured to face outward while in use,
the skin facing side being made of the body side sheet.

3. The steam-generative warming device according to claim 1, wherein the steam-generative warming device generates 5 to 50 mg steam/(cm$^2$·60 min).

4. The steam-generative warming device according to claim 1, wherein the capsaicin analog is represented by general formula (1):

wherein R is a C7-C12 alkyl or alkenyl group.

5. The steam-generative warming device according to claim 1, wherein the menthol is selected from the group consisting of L-menthol, DL-menthol, and mixtures thereof.

6. The steam-generative warming device according claim 1, wherein the steam generating element has a plan view area of 1.0 to 30 cm$^2$.

7. The steam-generative warming device according claim 1, wherein the steam generating element is covered with sheeting having air permeability in at least a part thereof, the sheeting comprising a first sheet configured to face the skin of a user while in use and a second sheet configured to face outward while in use, the second sheet having a larger air permeance than the first sheet.

8. The steam-generative warming device according to claim 1, configured to have heat generation characteristics such that the steam-generative warming device maintains a user's skin to which the steam-generative warming device is directly applied at a surface temperature of 38° to 43° C. for 1 to 5 hours.

9. The steam-generative warming device of claim 1, wherein the capsaicin analog/menthol mass ratio is 1/500 to 1/15000.

10. The steam-generative warming device of claim 9, wherein the capsaicin analog/menthol mass ratio is 1/1000 to 1/7000.

11. The steam-generative warming device of claim 2, wherein the capsaicin analog/menthol mass ratio is 1/500 to 1/15000.

12. The steam-generative warming device of claim 11, wherein the capsaicin analog/menthol mass ratio is 1/1000 to 1/7000.

\* \* \* \* \*